US008034910B2

United States Patent
Wang

(10) Patent No.: US 8,034,910 B2
(45) Date of Patent: Oct. 11, 2011

(54) SUMO FUSION PROTEIN EXPRESSION SYSTEM FOR PRODUCING NATIVE PROTEINS

(75) Inventor: Ting-Fang Wang, Taipei (TW)

(73) Assignee: Academia Sinica, Taiwan, Taipei (TW)

( * ) Notice: Subject to any disclaimer, the term of this patent is extended or adjusted under 35 U.S.C. 154(b) by 117 days.

(21) Appl. No.: 12/436,211

(22) Filed: May 6, 2009

(65) Prior Publication Data

US 2009/0280535 A1 Nov. 12, 2009

Related U.S. Application Data

(60) Provisional application No. 61/050,663, filed on May 6, 2008.

(51) Int. Cl.
*C07H 21/02* (2006.01)
*C12P 21/06* (2006.01)
*A23J 1/00* (2006.01)

(52) U.S. Cl. .......... 536/23.1; 435/69.1; 530/412

(58) Field of Classification Search .......... None
See application file for complete search history.

(56) References Cited

U.S. PATENT DOCUMENTS
6,872,551 B2   3/2005   Lima et al.
2009/0280531 A1 11/2009 Wang FOREIGN PATENT DOCUMENTS
EP         1961825      8/2008
WO    WO 2008/138578   11/2008

OTHER PUBLICATIONS

Guo et al., Protein tolerance to random amino acid change, 2004, Proc. Natl. Acad. Sci. USA 101: 9205-9210.*
Lazar et al., Transforming Growth Factor α: Mutation of Aspartic Acid 47 and Leucine 48 Results in Different Biological Activity, 1988, Mol. Cell. Biol. 8:1247-1252.*
Hill et al., Functional Analysis of conserved Histidines in ADP-Glucose Pyrophosphorylase from *Escherichia coli*, 1998, Biochem. Biophys. Res. Comm. 244:573-577.*
Wacey et al., Disentangling the perturbational effects of amino acid substitutions in the DNA-binding domain of p53., Hum Genet, 1999, vol. 104, pp. 15-22.*
Zuo et al., Enhanced expression and purification of membrane proteins by SUMO fusion in *Escherichia coli*, Journal of Structural and Functional Genomics, 2005, vol. 6, pp. 103-111.*
Henderson et al. (Cloning Strategy for Producing Brush-Forming Protein-Based Polymers, Biomacromolecules, 2005, vol. 6 (4), pp. 1912-1920.*
SUMOpro-3 Gene Fusion Technology by LifeSensors Inc (2007).*
SUMO Gene Fusion Technology by LifeSensors Inc (Oct. 2004).*
pET-24d Vectors from Novagen (last viewed on Jan. 20, 2010).*
Malakhov et al. SUMO fusions and SUMO-specific protease for efficient expression and purification of proteins, Journal of Structural and Functional Genomics, vol. 5, Nos. 1-2, 75-86.*
Lee et al. An improved SUMO fusions protein system for effective production of native proteins., Protein Science, E pub May 8, 2008, vol. 17, pp. 1241-1248.*

(Continued)

*Primary Examiner* — Alexander Kim
(74) *Attorney, Agent, or Firm* — Wolf, Greenfield & Sacks, P.C.

(57) ABSTRACT

A simple and efficient SUMO fusion protein expression system for producing native proteins.

23 Claims, 3 Drawing Sheets

OTHER PUBLICATIONS

Butt et al., "SUMO Fusion Technology for Difficult-to-Express Proteins", *Protein Expression and Purification 43*, 1-9, (2005).

Mossessova et al., "Ulp1-SUMO Crystal Structure and Genetic Analysis Reveal Conserved Interactions and a Regulatory Element Essential for Cell Growth in Yeast", *Molecular Cell*, vol. 5, pp. 865-876 (2000).

Kleid et al., "Cloned Viral Protein Vaccine for Foot-and-Mouth Disease: Responses in Cattle and Swine," *Science* 214:1125-1129 (1981).

Malten et al., "A Bacillus Megaterium Plasmid System for the Production, Export, and One-Step Purification of Affinity-Tagged Heterologous Levansucrase from Growth Medium," *Applied and Environmental Microbiology* 72(2):1677-1679 (2006).

\* cited by examiner

SUMO FUSION PROTEIN EXPRESSION SYSTEM FOR PRODUCING NATIVE PROTEINS

RELATED APPLICATION

This application claims priority to U.S. Provisional Application No. 61/050,663, filed on May 6, 2008, the content of which is hereby incorporated by reference in its entirety.

BACKGROUND OF THE INVENTION

Fusion protein technology, i.e., expressing in a host cell a target protein fused with a protein partner, allows for enhanced expression of the target protein, which is protected from degradation/mis-folding, easy to be purified/detected, and has improved solubility. The protein partner usually would interfere with the structural or functional properties of the target protein and therefore needs to be removed via, e.g., chemical or enzymatical cleavage, from a fusion protein to generate a free target protein. Cleavage of the protein partner remains the major disadvantage in conventional fusion technology as imprecise cleavage, which occurs frequently, results in failure to recover an active or structurally intact target protein.

The newly developed small-ubiquitin-related modifier (SUMO) fusion technology makes up for this disadvantage. In a SUMO fusion expression system, the fusion partner, i.e., a SUMO protein, can be precisely removed by a SUMO protease, thereby generating a native target protein. See, e.g., Butt et al., Protein Expression and Purification 43:1-9 (2005) and Mossessova et al., Molecular Cell 5:865-876 (2000).

SUMMARY OF THE INVENTION

The present invention relates to an improved SUMO fusion protein expression system that allows directional cloning of any target gene efficiently and producing a target protein having the exact amino acid sequence encoded by the target gene.

One aspect of this invention is an expression vector containing a first portion including a first nucleotide sequence that encodes a Smt3 protein, the 3' end of the first nucleotide sequence being replaced with a Sfo I site, and a second portion including another restriction site (e.g., XhoI, EcoRI, or BamHI). After inserting a DNA fragment, which or a portion of which encodes a protein of interest, into this expression vector via the Sfo I and the other restriction site, it expresses in a host cell a fusion protein containing, from the N-terminus to the C-terminus, the Smt3 protein and the protein of interest. Cleavage of the fusion protein by Ulp1 protease generates the protein of interest. This expression vector can further contain a nucleotide sequence encoding a protein tag (e.g., hexa-His, Maltose binding protein, N-utilizing substance A, Thioredoxin (Trx), Calmodulin-binding protein, Glutathione S-transferase, and α-factor) such that, after inserting the DNA fragment mentioned above, it expresses a fusion protein containing, from the N-terminus to the C-terminus, the protein tag, the Smt3 protein, and the protein of interest. The expression vector described above can be either linear or circular.

The term "restriction site" used herein refers to a nucleotide sequence recognizable by a restriction enzyme, or a nucleotide sequence generated by digestion of a restriction enzyme. "Ulp1 protease" is a polypeptide having the protease activity of *Saccharomyces cerevisiae* Ulp1 protease. It can be a full-length *Saccharomyces cerevisiae* Ulp1 protease or a fragment thereof (e.g., residues 403-621) that possesses protease activity, or a fusion protein containing the full-length or a fragment thereof, and a protein tag (e.g., a His-tag).

Another aspect of this invention is a method of producing a protein of interest by: (i) inserting into any of the expression vectors described above the DNA fragment also described above via the Sfo I restriction site and the other restriction site to form an expression construct, (ii) introducing the expression construct into a host cell, and (iii) expressing in the host cell a fusion protein containing, from the C-terminus to the N-terminus, the protein of interest, the Smt3 protein, and optionally, a protein tag. Preferably, the DNA fragment has a 5' end Gly codon (e.g., GGC) directly linked to a nucleotide sequence encoding the protein of interest. It can be prepared by sticky-end PCR so that no restriction enzyme digestion is needed before inserting it into the expression vector. The fusion protein thus produced can then be isolated via, e.g., affinity column, and subjected to Ulp1 protease cleavage to generate the protein of interest encoded exactly by its coding sequence, which preferably has the start codon ATG at its 5' end.

The term "producing a protein of interest" used herein refers to producing a protein of interest in either free form or fusion form. An "expression vector" is a plasmid containing, among other elements, a highly active promoter and one or more cloning sites downstream of the promoter. This plasmid is used to introduce into and express in a host cell a target gene inserted into the plasmid via the cloning sites. Cloning a target gene into an expression vector produces an expression construct.

Also within the scope of this invention is a method of purifying a protein of interest by: (i) providing a sample containing a fusion protein of, from the N-terminus to the C-terminus, a protein tag (e.g., hexa-His), a Smt3 protein, and a protein of interest, (ii) loading the sample to a protein-tag affinity column (e.g., Ni-NTA column) to allow binding of the fusion protein to the column, (iii) incubating the column with Ulp1 protease, which cleaves the fusion protein to produce the protein of interest, and (iv) eluting the protein of interest from the column.

The details of one or more embodiments of the invention are set forth in the description below. Other features or advantages of the present invention will be apparent from the following drawings and detailed description of several embodiments, and also from the appending claims.

BRIEF DESCRIPTION OF THE DRAWINGS

The drawings are first described.

DETAILED DESCRIPTION OF THE INVENTION

Figure 1:
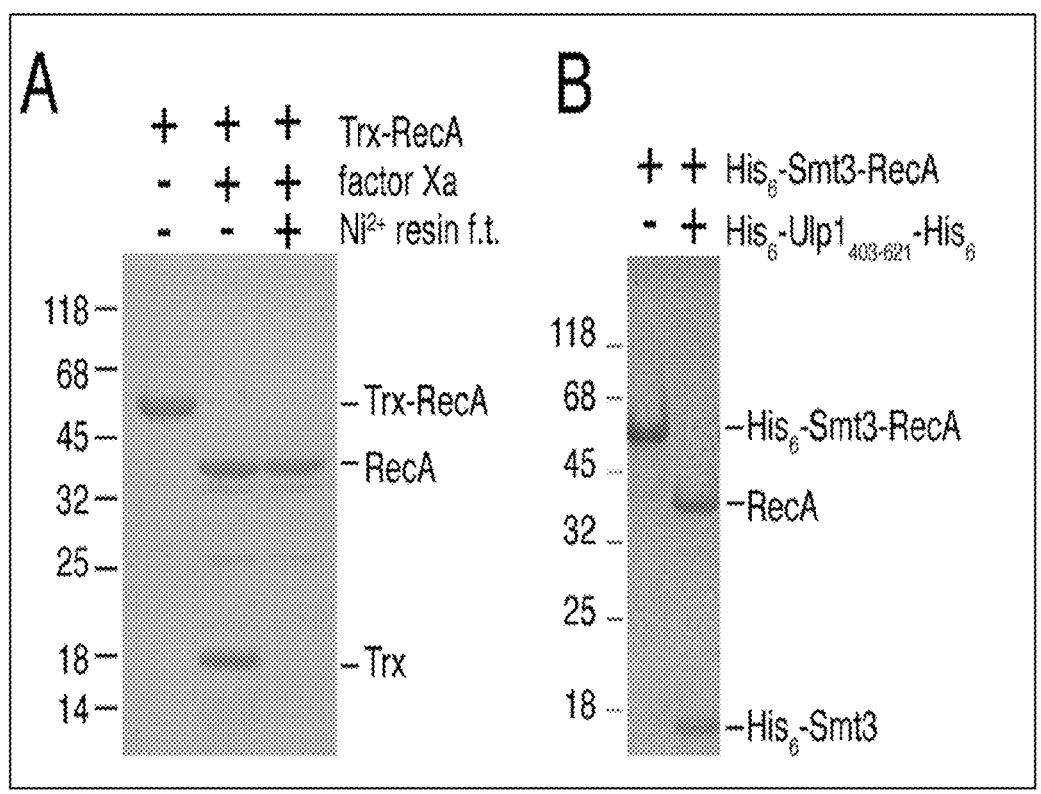
FIG. 1 is a photograph showing fusion proteins Trx-RecA and $His_6$-Smt3-RecA and the RecA protein in free form generated by cleaving the fusion proteins with factor Xa or $His_6$-$Ulp1_{403-621}$-$His_6$ in SDS-PAGE gels stained with Coomassie-blue. The molecular weight standards are shown on the left.

Described herein is a simple and efficient SUMO fusion protein expression system for producing a target protein having the exact amino acid sequence encoded by a coding sequence.

Described herein is a simple and efficient SUMO fusion protein expression system for producing a target protein having the exact amino acid sequence encoded by a coding sequence. This system utilizes an expression vector containing a nucleotide sequence encoding a Smt3 protein. A Smt3 protein can be the *Saccharomyces cerevisiae* Smt3 protein, the amino acid sequence of which is shown below:

```
                                        (SEQ ID NO: 1)
Amino acid sequence of Saccharomyces cerevisiae
Smt3:
MSDSEVNQEAKPEVKPEVKPETHINLKVSDGSSEIFFKIKKTTPLRRLME

AFAKRQGKEMDSLRFLYDGIRIQADQTPEDLDMEDNDIIEAHREQIGG
```

A Smt3 protein can also be a functional variant of the yeast Smt3 mentioned above, which is a polypeptide that shares a high sequence homology with Smt3 (e.g., sequence identity at least 85%, 90%, 95%, 98%, or 99%). When fused with a target protein, a functional variant of yeast Smt3 can be cleaved by Ulp1 protease to generate a free Smt3 protein having the mature C-terminus of yeast Smt3, i.e., -Gly-Gly at the C-terminus of the free Smt3 protein. See Mossessova et al., Mol. Cell 5:865-876 (2000). In another example, a Smt3 protein is a fusion protein containing yeast Smt3 or its functional variant and a small protein tag, e.g., a hexa-His tag. The amino acid sequence of a His-tag fused yeast Smt3 protein is shown below:

```
                                        (SEQ ID NO: 2)
Amino acid sequence of His-tag-Saccharomyces
cerevisiae Smt3 fusion protein:
MGSSHHHHHHSSGLVPRGSASMSDSEVNQEAKPEVKPEVKPETHINLKVS

DGSSEIFFKIKKTTPLRRLMEAFAKRQGKEMDSLRFLYDGIRIQADQTPE

DLDMEDNDIIEAHREQIGG
```

To prepare the expression vector of this invention, the 3' end of the nucleotide sequence that encodes a Smt3 protein is replaced with a Sfo I restriction site for cloning downstream thereof a DNA fragment that encodes a target protein. In one example, the 3' end of the Smt3 coding sequence, i.e., GGTGGT (encoding Gly-Gly), is replaced with GGCGCC (a Sfo I site, encoding Gly-Ala). In another example, the GGTGGT sequence is replaced with GGTGGCGCC (encoding Gly-Gly-Ala). Preferably, this expression vector also includes a nucleotide sequence encoding a protein tag (e.g., His-tag) linked to the 5' end of the nucleotide sequence encoding Smt3.

A DNA fragment described above, coding for a target protein, can be prepared by conventional methods. Preferably, the DNA fragment is produced by sticky-end PCR such that it can be inserted into the expression vector mentioned above without being digested by restriction enzymes. After inserting the DNA fragment into the expression vector, the junction region of the Smt3 coding sequence and the DNA fragment can have the sequence of GGCGGCATG (encoding -Gly-Gly-M-), in which ATG is the start codon of the protein encoded by the DNA fragment. The resultant expression construct expresses in a host cell a fusion protein containing the Smt3 protein and the target protein, and preferably, a protein tag. The fusion protein can be purified by, e.g., affinity column and then cleaved by a Ulp1 protease, which precisely cleaves after the -Gly-Gly- residues, thereby yielding the target protein having the exact amino acid sequence corresponding to its coding sequence. Alternatively, Ulp1 protease cleavage can be performed when the fusion protein is still bound to the affinity column.

Several embodiments of this invention are described in the following examples and also in Lee et al, Protein Science, 17(7):1241-1248 (2008).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference.

EXAMPLE 1

Production of Fusion Protein Containing Smt3 and *Escherichia coli* RecA Protein The *Saccharomyces cerevisiae* Smt3 gene was cloned into pET32-Xa/LIC vector (Novagen, USA), downstream of the $His_6$-tag contained in this vector to produce a $His_6$-Smt3 expression vector.

The open reading frame of the *Escherichia coli* RecA protein was first cloned into the pET32-Xa/LIC vector (Novagen, USA) to generate a thioredoxin(Trx)-RecA expression construct. The DNA fragment encoding the Trx protein was then replaced by that of the $His_6$-Smt3 protein. As a result, the open reading frame of the *Escherichia coli* RecA protein is downstream of and in-frame with the $His_6$-Smt3 gene to produce a SUMO-RecA expression construct (pSUMO-RecA).

pSUMO-RecA as described above was transformed into JM109(DE3)-competent cells, which were cultured overnight at 37° C. in the presence of 100 mg/L ampicillin to produce an overnight culture (15 mL). The overnight culture was then transferred to 1 L fresh Luria-Bertani medium, grew at 37° C. until it reached an $OD_{600}$ value of about 0.5-0.6, and IPTG (1 mM) was then added to the *E. coli* culture to induce protein expression. The induced cells were grown at 20° C. for 12 h, harvested, and then centrifuged at 9,000×g for 30 min. The cell pellet thus obtained were lyzed according to the method described in Wang et al., J. Biol. Chem 268:26049-26051 (1993), except that a different lysis buffer [50 mM Tris-HCl (pH 7.4), 300 mM NaCl, 0.2 mM EGTA (pH 8.0)] was used here to prevent non-specific association of $His_6$-Smt3-RecA with bacterial DNA. After centrifugation, the soluble fraction thus obtained was mixed with 2 mL of $Ni^{2+}$ resins (Amersham, USA) to which the $His_6$-Smt3-RecA fusion protein binds. The $Ni^{2+}$ resins were washed three times with 30 mL of wash buffer [50 mM Tris-HCl (pH 7.4), 300 mM NaCl, 0.2 mM EGTA (pH 8.0), 40 mM imidazole (pH 8.0)] and the fusion protein bound to them were then eluted.

The His6-Smt3-RecA fusion protein and the free RecA protein released from the fusion protein via Ulp1 protease cleavage were detected on an SDS-PAGE gel stained with Coomassie-blue. See FIG. 1. A single band representing free RecA was detected, indicating that Ulp1 protease cleaved at only one site in the His6-Smt3-RecA fusion protein. Fusion protein Trx-RecA, expressed from pET32-Xa/LIC-Trx-RecA expression vector, and free RecA released from this fusion protein via factor Xa cleavage, were also detected by SDS-PAGE analysis. Multiple bands representing the released RecA proteins were detected, indicating that factor Xa cleavage took place at unexpected sites in the Trx-RecA fusion protein. See also FIG. 1.

EXAMPLE 2

Preparation of Free RecA protein from His$_6$-Smt3-RecA Fusion Protein Via a One-Column Approach Described below is a one-column approach to produce free RecA protein from the His$_6$-Smt3-RecA fusion proteins produced by the method described in Example 1 by Ulp1 cleavage.

Ulp 1$_{403-621}$, a fragment of *Saccharomyces cerevisiae* Ulp1 protein (amino acid residues 403-621), has been shown to cleave a C-terminal tagged yeast Smt3 in vitro, producing its mature form (i.e., C-terminal "Gly-Gly"). See Mossessova et al., Mol. Cell 5:865-876 (2000). The open reading frame of Ulp1$_{403-621}$ was cloned into the pET28a vector (Novagen, USA) to generate an expression vector, which was then transformed into *E. coli* cells to express a His$_6$-Ulp1$_{403-621}$-His$_6$ fusion protein. This recombinant enzyme, soluble in water, was purified from the crude extract of the transformed *E. coli* cells, using Ni$^{2+}$ resins. The final yield was ~20 mg/L *Escherichia coli* culture. The protein migrated as a single band on an SDS-PAGE gel stained with Coomassie blue, and with >99% purity as determined by densitometry. The His$_6$-Ulp1$_{403-621}$-His$_6$ fusion protein exhibited a high affinity to Ni$^{2+}$-resin and did not release from Ni$^{2+}$-resins unless more than 300 mM imidazole or 100 mM EDTA was added to an elution buffer.

An *E. coli* crude extract containing the His$_6$-Smt3-RecA fusion protein described in Example 1 was loaded to a column containing Ni$^{2+}$-resins, which were then washed three times with 30 mL of the wash buffer also described in Example 1. Without elution, the Ni$^{2+}$-column, bound with the His$_6$-Smt3-RecA fusion protein, was then loaded with His$_6$-Ulp1$_{403-621}$-His$_6$ to allow proteolytic cleavage of the His$_6$-Smt3-RecA fusion protein. The free RecA protein thus generated was then eluted from the Ni$^{2+}$-resins. The final yield was ~10 mg proteins per liter of cell culture.

The N-terminus of the eluted free RecA protein was examined by Edman degradation to confirm that the Ulp1 cleavage was precise. Results thus obtained indicate that the N-terminal sequence of the RecA protein is identical to that encoded by its gene. The molecular weight of the purified RecA, determined by mass spectrometry, was around 37,843 Da, which is very close to the predicted molecular weight of native RecA protein, i.e. 37,842 Da. This purified RecA protein was shown under electron microscopy to form helical filaments on a circular ds-ΦX174 substrate, indicating that the purified RecA proteins have no apparent polymerization defect.

The biological activities of the purified RecA protein was tested as follows. First, an electrophoretic mobility shift assay was performed to examine whether the RecA protein was capable of binding to DNA, following the method described in Chen et al., Proc. Natl. Acad Sci USA 101:10572-10577 (2004). Incubation of 10 μM RecA with 8 μM (in bp) of ds-ΦX174 DNA resulted in a substantial decrease in the electrophoretic mobility of ds-ΦX174. Six oligonucleotides, i.e., (CT)$_{20}$, (CA)$_{20}$, (GT)$_{20}$, (GA)$_{20}$, (AT)$_{20}$, and (CG)$_{20}$ described in Biet et al., Nucleic Acids Res 27:596-600 (1999), were used to determine the preference of the RecA protein for binding to double-strand (ds) or single-strand (ss) DNAs. 80 μM of each of the oligonucleotides was incubated with the RecA protein in the presence of circular ds-ΦX174 (8 μM) DNA and then a mobility shift assay was performed to examine the binding between the RecA protein and the ds- or ss-DNAs. Results thus obtained show that all six oligonucleotides competed against ds-ΦX174 for binding to the RecA protein. The purified RecA protein exhibited no obvious preference for binding to ssDNA than to dsDNA, as addition of oligonucleotide (CT)$_{20}$ at low concentrations (2, 4, or 8 μM) resulted no significant increase in the electrophoretic mobility of ds-ΦX174.

Second, a D-loop formation assay was performed to determine whether the purified RecA protein could promote a homology-dependent strand exchange reaction, a bioactivity possesses by native RecA. Briefly, the purified RecA protein (1 μM) was preincubated with 3 μM (in nucleotides) 5' $^{32}$P end-labeled P1656 ssDNA for 5 min at 37° C. in the presence of 1 mM magnesium acetate and 2 mM AMP-PNP. A D-loop formation reaction was initiated by the addition of an equal volume (10 μL) of a solution containing a supercoiled double-stranded (ds) DNA plasmid GW1 (20 μM in base pairs). See Chen et al. Nucleic Acids Res. 35:1787-1801 (2007); Chen et al., PLos ONE 2:e858 (2007); and Chen et al., Proc Natl Acad Sci USA 101:10572-10577 (2004). Five minutes later, the reaction was terminated by addition of 2 μL SDS (5.5%) and proteinase K (6 mg/ml) for 5 min to remove the proteins. The DNAs contained in the reaction mixture were detected by electrophoresis for 2 h at 4 V/cm on a 0.8% agarose gel in Tris-acetate-EDTA buffer (40 mM Tris, 1 mM Na$_2$-EDTA, and 20 mM acetic acid, pH 8.0). A phosphorimage of the agarose gel was taken to show the D-loop formation in the presence of RecA proteins. See Lee et al., Biochem Biophys Res. Commun 323:845-851 (2004). Results thus obtained indicate that the purified RecA, just like native RecA, promoted D-loop formation.

Finally, the ssDNA-activated ATPase activity of the purified RecA protein was tested following the method described in Lee et al., Biochem Biophys Res Commun 323:845-851 (2004). In the presence or absence of ss-ΦX174 DNA, the RecA protein released $^{32}$P inorganic phosphate from γ-$^{32}$P-ATP, indicating that it possessed the ssDNA-activated ATPase activity.

In sum, the RecA protein produced in the SUMO fusion system described herein and purified by the one-column approach also described herein possessed identical physical and biological features to the native RecA protein.

EXAMPLE 3

Figure 2:
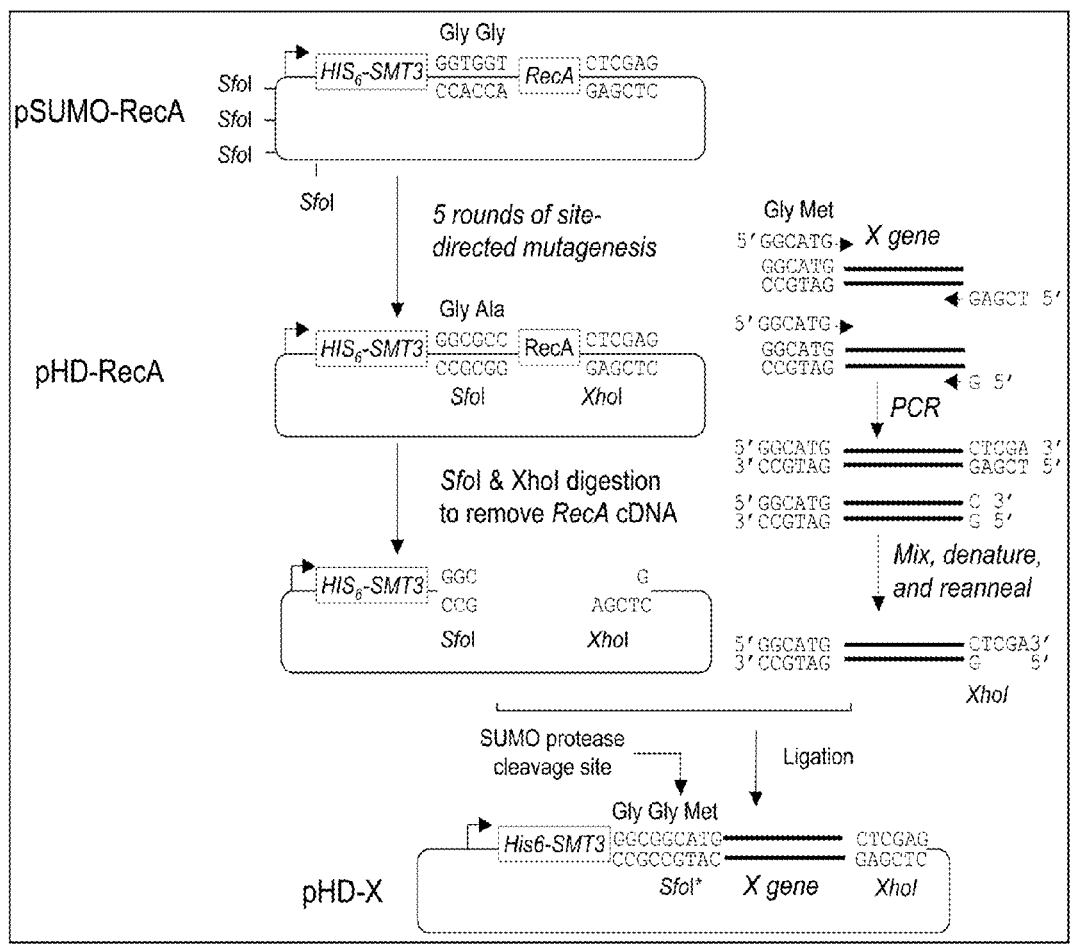
FIG. 2 is a diagram showing the process of generating a new SUMO fusion protein expression vector pHD.

Construction of SUMO Fusion Protein Expression Vector pHD pHD, a SUMO fusion protein expression vector, was constructed as illustrated in FIG. 2. First, the pSUMO-RecA vector described in Example 1 was subjected to five rounds of site-directed mutagenesis reactions to mutate the four Sfo I (5'GGCGCC3') restriction sites in the backbone of pET32-Xa/LIC to either 5'GGCTCC3' or 5'GGCACC3', and to create a new Sfo I restriction site at the SUMO protease cleavage site by mutating "GGTGGT," encoding the two C-terminal residues 'GlyGly' of Smt3 to "GGCGCC", encoding 'GlyAla'. Next, the mutated pSUMO-RecA vector thus produced was subjected to Sfo I and XhoI digestion to remove the DNA fragment encoding RecA, resulting in a linear vector pHD, one end of which is a Sfo I site and the other end of which is a XhoI site.

This linear vector can be inserted with any target gene prepared by the sticky-end PCR cloning method described in Shih et al. Protein Sci. 11:1714-1719 (2002) via the Sfo I site and the XhoI site. As illustrated in the right panel of FIG. 2, a target gene can be amplified by sticky-end PCR cloning technology, which requires two PCR reactions in two separate tubes. Both PCR products are purified and mixed equally. After denaturation and renaturation, 50% of the final products carry one Sfo I blunt end and one XhoI cohesive end, and are ready for ligation even without restriction digestion of the PCR products. After ligating the linear vector pHD with the DNA fragment prepared by sticky-end PCR, a new "GlyGly" SUMO cleavage site is generated right before the first amino acid codon of the target gene (see FIG. 2).

EXAMPLE 4

Producing Rad51 VP 1 and VP3 Proteins Using Expression Vector pHD

Figure 3:
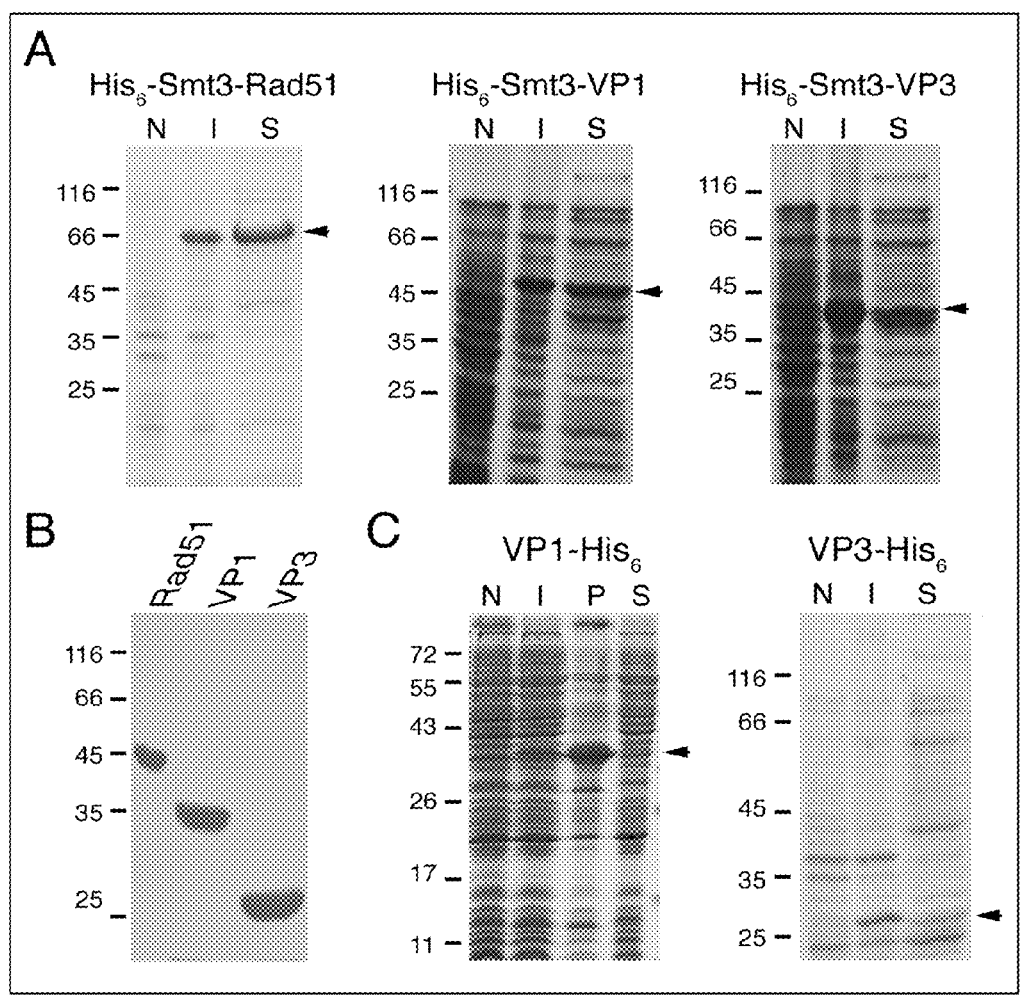
FIG. 3 is a photograph showing fusion proteins $His_6$-Smt3-Rad51, $His_6$-Smt3-HFDV-VP 1, and $His_6$-Smt3-FMD-VP3 expressed from expression vectors pHD-Rad51, pHD-HFDV-VP1, and pHD-FMD-VP3 in SDS-PAGE gels stained with Coomassie-blue. N: whole cell lysates derived from uninduced cells; I: whole cell lysate derived from IPTG-induced cells; and S: soluble proteins derived from IPTG-induced cells.

Rad 51, capsid protein VP1 of Hand-foot-and-mouth disease virus EV71 (HFMDV-VP1), and capsid protein VP3 of foot-and-mouth disease virus (FMDV-VP3) are all known to be very poorly expressed in *E. coli* using conventional recombinant technology. See Van Komen et al., Methods in Enzymol. 408:445-462 (2006) and also see FIG. 3, panel C.

Genes encoding the three proteins mentioned above were first amplified by sticky-end PCR and then inserted into vector pHD via the Sfo I and XhoI restriction sites. The expression vectors thus formed were transformed into host *E. coli* cells, in which soluble fusion proteins $His_6$-Smt3-Rad51, $His_6$-Smt3-VP1, and $His_6$-Smt3-VP3 were expressed. See FIG. 3, panel A. These fusion proteins were subjected to cleavage by $His_6$-Ulp1$_{403-621}$-$His_6$. See also FIG. 3, panel B.

The final yield of Rad51 was ~10 mg per liter of *Escherichia coli* culture. Determined by mass spectrometry, this recombinant protein has a molecule weight of 42,964 Da, very close to the predicted molecule weight of native Rad51, i.e., 42,963 Da. Edman degradation analysis confirmed that the Rad51 protein produced in the SUMO fusion system described herein has the exact N-terminus amino acid residue as its native counterpart.

HFMDV-VP1 and FMDV-VP3, when expressed as fusion proteins with Hexa-His tag only, were insoluble. See FIG. 3, panel C. When expressed in the SUMO fusion system described herein, both $His_6$-Smt3-VP1 and $His_6$-Smt3-VP3 proteins were soluble. See FIG. 3, panel A. Authentic VP1 and Vp3 proteins were produced after cleavage of the fusion proteins by $His_6$-Ulp1$_{403-621}$-$His_6$. See FIG. 3, Panel B. Edman degradation analysis confirmed that the N-termini of purified HFDV-VP1 and FMDV-VP3 were identical to those of the native HFDV-VP1 and FMDV-VP3. Mass spectrometry analysis revealed that the molecular weights of HFMDV-VP1 and FMDV-VP3 were 32,829 Da and 23,816 Da, respectively. The predicted molecular weights of these two proteins are 32,744 Da and 23,817 Da.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. An expression vector comprising:
   a first portion including a first nucleotide sequence that encodes a small ubiquitin-related modifier protein (Smt3) having an amino acid sequence at least 85% identical to SEQ ID NO:1, the 3' end of the first nucleotide sequence being replaced with a Sfo I restriction site; and
   a second portion including another restriction site, wherein the expression vector, upon insertion of a DNA fragment encoding a protein of interest via the Sfo I restriction site and said another restriction site, expresses a fusion protein containing, from the N-terminus to the C-terminus, the Smt3 protein and the protein of interest, and cleaving the fusion protein by Ubl-specific protease 1 (Ulp1) produces the protein of interest.

2. The expression vector of claim 1, wherein the first portion further includes a second nucleotide sequence that encodes a protein tag, and wherein, the expression vector, upon insertion of a DNA fragment encoding a protein of interest via the Sfo I restriction site and said another restriction site, expresses a fusion protein containing, from the N-terminus to the C-terminus, the protein tag, the Smt3 protein, and the protein of interest.

3. The expression vector of claim 2, wherein the protein tag is selected from the group consisting of hexa-His, Maltose binding protein, N-utilizing substance A, Thioredoxin, Calmodulin-binding protein, Glutathione S-transferase, and α-factor.

4. The expression vector of claim 3, wherein the protein tag is hexa-His.

5. The expression vector of claim 2, wherein said another restriction site is XhoI.

6. The expression vector of claim 2, wherein the vector is a linear molecule having one end being the Sfo I restriction site and the other end being said another restriction site.

7. The expression vector of claim 1, wherein said another restriction site is XhoI.

8. The expression vector of claim 1, wherein the vector is a linear molecule having one end being the Sfo I restriction site and the other end being said another restriction site.

9. The expression vector of claim 1, wherein the Smt3 has an amino acid sequence at least 90% identical to SEQ ID NO:1.

10. The expression vector of claim 9, wherein the Smt3 has an amino acid sequence at least 95% identical to SEQ ID NO:1.

11. The expression vector of claim 10, wherein the Smt3 has the amino acid sequence of SEQ ID NO:1.

12. The expression vector of claim 1, wherein the expression vector further comprises the DNA fragment inserted via the Sfo I restriction site and said another restriction site.

13. A method of producing a protein of interest, comprising:
   providing the expression vector of claim 1, in which a DNA fragment is inserted via the Sfo I restriction site and said another restriction site, the DNA fragment encoding a protein of interest,
   introducing the expression construct into a host cell, and
   producing in the host cell a fusion protein containing, from the N-terminus to the C-terminus, the Smt3 protein, and the protein of interest.

14. The method of claim 13, wherein the DNA fragment contains a 5' end Gly codon directly linked to a nucleotide sequence that encodes the protein of interest.

15. The method of claim 14, wherein the DNA fragment has a 5' end sequence GGCATG, in which GGC is the Gly codon and ATG is the 5' end of the nucleotide sequence encoding the protein of interest.

16. The method of claim 14, wherein the DNA fragment is prepared by sticky-end PCR.

17. The method of claim 13, wherein said another restriction site is XhoI.

18. The method of claim 13, further comprising isolating the fusion protein from the host cell and cleaving it with Ubl-specific protease 1 (Ulp1), thereby producing the protein of interest.

19. The method of claim 18, wherein the Ulp1 protease is $His_6$-$Ulp1_{403-621}$-$His_6$.

20. The method of claim 13, wherein the expression vector further includes a second nucleotide sequence encoding a protein tag such that the fusion protein expressed from the expression vector contains the protein tag at its N-terminus.

21. The method of claim 20, wherein the protein tag is selected from the group consisting of hexa-His, Maltose binding protein, N-utilizing substance A, Thioredoxin, Calmodulin-binding protein, Glutathione S-transferase, and α-factor.

22. The method of claim 20, further comprising:
   loading a sample prepared from the host cell that contains the fusion protein to a protein-tag affinity column to allow binding of the fusion protein to the column,
   incubating the column with Ub1-specific protease 1 (U1p1), which cleaves the fusion protein to produce the protein of interest, and
   eluting the protein of interest from the column.

23. The method of claim 22, wherein the protein tag is hexa-His and the protein-tag affinity column is a Ni-NTA column.

* * * * *

SEQUENCE LISTING

<160> NUMBER OF SEQ ID NOS: 2

<210> SEQ ID NO 1
<211> LENGTH: 98
<212> TYPE: PRT
<213> ORGANISM: Saccharomyces cerevisiae

<400> SEQUENCE: 1

Met Ser Asp Ser Glu Val Asn Gln Glu Ala Lys Pro Glu Val Lys Pro
1               5                   10                  15

Glu Val Lys Pro Glu Thr His Ile Asn Leu Lys Val Ser Asp Gly Ser
            20                  25                  30

Ser Glu Ile Phe Phe Lys Ile Lys Lys Thr Thr Pro Leu Arg Arg Leu
        35                  40                  45

Met Glu Ala Phe Ala Lys Arg Gln Gly Lys Glu Met Asp Ser Leu Arg
    50                  55                  60

Phe Leu Tyr Asp Gly Ile Arg Ile Gln Ala Asp Gln Thr Pro Glu Asp
65                  70                  75                  80

Leu Asp Met Glu Asp Asn Asp Ile Ile Glu Ala His Arg Glu Gln Ile
                85                  90                  95

Gly Gly

<210> SEQ ID NO 2
<211> LENGTH: 119
<212> TYPE: PRT

-continued

<213> ORGANISM: Saccharomyces cerevisiae

<400> SEQUENCE: 2

```
Met Gly Ser Ser His His His His His His Ser Ser Gly Leu Val Pro
1               5                   10                  15

Arg Gly Ser Ala Ser Met Ser Asp Ser Glu Val Asn Gln Glu Ala Lys
            20                  25                  30

Pro Glu Val Lys Pro Glu Val Lys Pro Glu Thr His Ile Asn Leu Lys
        35                  40                  45

Val Ser Asp Gly Ser Ser Glu Ile Phe Phe Lys Ile Lys Lys Thr Thr
    50                  55                  60

Pro Leu Arg Arg Leu Met Glu Ala Phe Ala Lys Arg Gln Gly Lys Glu
65                  70                  75                  80

Met Asp Ser Leu Arg Phe Leu Tyr Asp Gly Ile Arg Ile Gln Ala Asp
                85                  90                  95

Gln Thr Pro Glu Asp Leu Asp Met Glu Asp Asn Asp Ile Ile Glu Ala
            100                 105                 110

His Arg Glu Gln Ile Gly Gly
            115
```